United States Patent [19]
DeStefano et al.

[11] Patent Number: 6,135,628
[45] Date of Patent: *Oct. 24, 2000

[54] METHOD AND APPARATUS FOR HOMOGENIZING AEROSOL FORMULATIONS

[75] Inventors: George A. DeStefano; Daniel P. McNamara; Paul D. Jager, all of Waterbury; Jadwiga Jachowicz, Bethel, all of Conn.

[73] Assignee: Boehringer Ingelheim Pharmceuticals, Inc., Ridgefield, Conn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/723,520

[22] Filed: Sep. 30, 1996

Related U.S. Application Data
[60] Provisional application No. 06/005,463, Oct. 13, 1995.

[51] Int. Cl.[7] .................. B01F 5/06; B01F 3/04; B01F 3/06
[52] U.S. Cl. ............ 366/176.1; 366/162.4; 516/8.1; 516/6; 261/41.5; 422/281; 422/282
[58] Field of Search ............ 366/176.1, 162.4; 252/305; 516/8.1, 6; 261/41.5; 422/281, 282

[56] References Cited

U.S. PATENT DOCUMENTS

| | | | |
|---|---|---|---|
| 4,405,489 | 9/1983 | Sisbarro | 252/305 |
| 4,533,254 | 8/1985 | Cook et al. | 366/176.1 |
| 4,908,154 | 3/1990 | Cook et al. | 252/314 |
| 4,971,788 | 11/1990 | Tabibi et al. | 424/49 |
| 5,270,305 | 12/1993 | Palmer | 514/171 |
| 5,603,918 | 2/1997 | McNamara | 424/46 |

FOREIGN PATENT DOCUMENTS

| | | |
|---|---|---|
| 369967 | 6/1930 | Belgium . |
| 0335189 | 10/1989 | European Pat. Off. . |
| 426734 | 6/1967 | Switzerland . |
| 9111496 | 8/1991 | WIPO . |
| 9614925 | 5/1996 | WIPO . |

OTHER PUBLICATIONS

"M–110Y High Pressure Microfluidizer(R) Processor", Technical Bulletin 110Y–2, (Microfluidics International Corp., Newton, MA, USA. copyright 1994). Month Unknown.

"M–110E Electric–Hydraulic Laboratory Microfluidizer(R)", Technical Bulletin, (Microfluidics Corporation, Newton, MA, USA, copyright 1993). Month Unknown.

"Microfluidizer(R) Processing Equipment, Product catalog", (Microfluidics Corp., Newton, MA, Copyright 1993). Month Unknown.

European Search Report, May 30, 1997, The Hague, Examiner Dugdale, G., Application No. EP96116310.

*Primary Examiner*—Richard D. Lovering
*Assistant Examiner*—Daniel S. Metzmaier
*Attorney, Agent, or Firm*—Hedman, Gibson & Costigan, P.C.

[57] ABSTRACT

A method and apparatus for homogenizing and micronizing aerosol formulations. The method includes the steps of homogenizing and micronizing an aerosol formulation at ambient temperature in a closed apparatus where the entire apparatus is maintained under elevated pressure. The apparatus includes a closed loop containing a reaction vessel, a homogenizer and a fluid conduit interconnecting the reaction vessel and the homogenizer. The homogenizer includes an interaction chamber and an intensifier pump. The interaction chamber includes a stream splitter for separating a stream of aerosol formulation components into two streams and an impaction chamber for recombining the stream.

7 Claims, 6 Drawing Sheets

METHOD AND APPARATUS FOR HOMOGENIZING AEROSOL FORMULATIONS

The benefit of provisional application Ser. No. 60/005,463, filed Oct. 13, 1995, is hereby claimed.

FIELD OF THE INVENTION

The present invention relates generally to a method and apparatus for homogenizing a mixture containing a volatile, low-boiling substance and, more specifically, to a method and apparatus for homogenizing aerosol formulations including low-boiling propellants such as hydrofluorocarbons. The invention further relates to a method and apparatus which can both micronize particles of active substance in an aerosol formulation and homogenize the formulation.

BACKGROUND OF THE INVENTION

An aerosol is a gaseous suspension of fine solid or liquid particles. An aerosol formulation, in turn, is one which comprises a solution or suspension of an active ingredient in a liquid which consists of a propellant and an any necessary solvent or surfactant. The propellant will generally be a low boiling liquid, which volatilizes under ambient conditions of temperature and pressure. The formulation is held, under pressure, in a container, and released from the container through a valve, to form an aerosol spray.

A great many substances are designed to be delivered in the form of aerosol sprays, such as, for example, medicaments, insecticides and paints. While the present invention is applicable to the preparation of aerosol formulations in general, it is especially applicable to the preparation of aerosol formulations of medicaments which are intended to be administered, by inhalation, in the form of metered doses of aerosol spray, using a dispensing device called a metered dose inhaler (MDI).

To deliver an aerosol spray of uniform composition, an aerosol formulation should be as homogeneous as possible. For an aerosol formulation which comprises a solid as its active ingredient, the active ingredient should be finely divided and it, together with the propellant and other formulation components, such as solvent or surfactant, should form a uniformly dispersed suspension. Thus, it is generally necessary to subject an aerosol formulation to some sort of homogenization procedure prior to packaging.

As aerosol formulations contain propellants which become gaseous at normal temperature and pressure (about 20° C. and 1 atmosphere), the homogenization of an aerosol formulation can be problematical. In order to avoid volatilization, an aerosol propellant must be handled at either elevated pressure or at a temperature which is below its boiling point.

An homogenization apparatus, of the sort typically used for the homogenization of an aerosol formulation in accordance with current practice, comprises a containment vessel and a propeller-like rotor which impels liquid contained in the vessel against a stator, causing the liquid to be homogenized. Currently available homogenizers of this design (rotor/stator homogenizers) are not adapted to operate with the contents of the containment vessel under substantially elevated pressure. That is to say, a homogenization apparatus of the rotor/stator design can operate only at ambient pressure or at slightly elevated pressure; it cannot operate at an elevated pressure which would be sufficient to keep a volatile material in its liquid state. Thus, a rotor/stator homogenizer can only be used to homogenize a mixture which contains a low-boiling, volatile propellant if the process is carried out at a temperature below the boiling point of the propellant. Where this is not desired or possible, as in cases wherein the constituents of the aerosol formulation are not sufficiently miscible at reduced temperature, another expedient can be resorted to. In such situations, a non-volatile product concentrate, consisting of the active ingredient and a relatively high boiling, relatively non-volatile liquid is first produced. As the product concentrate is relatively non-volatile, it can be homogenized using a rotor/stator homogenizer at ambient temperature and pressure. Once homogenized, the product concentrate can be admixed with the propellant, under pressure, to form an homogenous aerosol formulation.

Thus, for example, it is known in the pharmaceutical art that an inhalation aerosol formulation of a medicament, containing a relatively low boiling chloroflurocarbon (CFC) as propellant, such as, for example CFC 12 ($CCl_2F_2$, $\underline{T}_b$/° C.=−29.8) or CFC 114 ($C_2Cl_2F_4$, $\underline{T}_b$/° C.=3.8), can be made by first first preparing a product concentrate which comprises the active medicament as a finely divided solid, a relatively high boiling CFC, such as for example CFC 11 ($CCl_3F$, $\underline{T}_b$/° C.=23.75) and a surfactant or suspending agent (e.g. soy lecithin, oleic acid, Span®, etc.). This product concentrate can be homogenized at ambient temperature and pressure, using a rotor/stator homogenizer. Once homogenized, the product concentrate and the relatively low boiling CFC propellant are introduced into a pressure vessel, where they are mixed to form a completed and homogenous formulation. The completed formulation is then filled into dispensing devices, such as MDI's, working either under elevated pressure and ambient temperature (by back-filling through the valves of capped containers), or at reduced temperature and ambient pressure (wherein the containers are filled and then capped).

In the aforementioned formulation, the relatively high boiling CFC serves three important and distinct functions. First, it serves as a solvent for the suspending agent, such as soy lecithin. To ensure accurate, reproducible dosing, it is necessary for the suspending agent to be completely soluble in the product concentrate (in which the high boiling CFC is the only CFC present) and in the entire formulation (in which both high and low boiling CFCs are present). Second, with regard to its interaction with the solid drug particles, the high boiling CFC serves as a dispersion medium. Third, it contributes to the overall vapor pressure of the final formulation. The pressure of the formulation is one of the variables that affects the optimization of active ingredient deposition in the lungs of a patient and, therefore, the efficacy of the formulation. In this context, the relatively high boiling CFC is referred to as a propellant, because the final vapor pressure of the formulation is the result of the partial pressure contributions of all of the CFCs used in the formulation.

Recent environmental concerns regarding the use of CFC propellants have led to the substitution of hydrofluorocarbon alkane (HFA) propellants in place of traditional CFCs. It has been found that the above-described methods for preparing aerosol formulations, in which homogenization is accomplished using a rotor/stator homogenizer, at ambient temperature and pressure, cannot generally be used to make HFA-based formulations.

In particular, there are no acceptable high boiling HFAs which can be used to create a non-volatile product concentrate, as is done in the case of the above-described CFC formulation, in which CFC 11 is used. Accordingly, a homogenous mixture of a low boiling HFA, the active drug, a surfactant, and other formulation constituents must be made. It will be readily apparent that the homogenization of a formulation comprising a low boiling HFA must either be carried out at elevated pressure or reduced temperature because the low boiling HFA would otherwise evaporate. However, it is not always possible to carry out the homogenization at reduced temperature since many of the surfactants which are compatible with HFAs are not soluble in the HFA formulation at reduced temperature. Therefore, the homogenization must be carried out at elevated pressure.

Unfortunately, as mentioned before, rotor/stator homogenizers do not presently exist which are adapted to operate under sufficient pressure to prevent the volatilization of a low boiling constituent, such as a propellant. Accordingly, existing techniques cannot be used to homogenize a formulation containing a low boiling constituent, such as an HFA propellant, at ambient temperatures.

As further background, it should be understood that where solid particles of active substance are to be suspended in an aerosol formulation such particles must have a very small and substantially uniform particle size. That is to say, the particles of active ingredient, in order to form an homogenous suspension, must be micronized. Such micronization is usually accomplished by a milling operation which is carried out before the active substance is incorporated into the formulation. Such milling operations are undesirable in that they tend to produce an airborne dust of active substance which represents a costly loss of active material, and which contaminants the production environment, making housekeeping more difficult and creating a possible hazard for workers. Although desirable, the prior art does not provide a method or apparatus whereby a solid active substance can be micronized after it has been incorporated into an aerosol formulation, for example during the homogenization step, so that prior milling can be avoided.

SUMMARY OF THE INVENTION

In accordance with the aforementioned and other objects which will become subsequently apparent, the present invention is directed to a closed, pressurizable system for homogenizing aerosol formulations including the following components: (1) a pressurizable mixing vessel having inlet and outlet means; (2) a homogenizer disposed in fluid communication with the reaction vessel, said homogenizer including a plurality of nozzles having elongated orifices to eject under pressure sheets of the liquid to be homogenized, said nozzles being arranged to effect turbulent jet interaction of said sheets along a common jet interaction front and said sheets being ejected by said nozzles into a low-pressure zone filled with said liquid of the sheets along a common liquid jet interaction front and said sheets being ejected by said nozzles into a low-pressure zone filled with said liquid further creating turbulent jet interaction along a common boundary essentially defined and formed by said mixture in said low pressure zone and by said sheets ejected into said low pressure zone; jet interaction chamber-defining means arranged to provide said low pressure zone of said liquid system in which said turbulent jet interaction is effected; pump means for delivering said liquid system under pressure to said nozzles; and (3) fluid conduits running from said outlet of said mixing vessel to the homogenizer and from the homgenizer back to the inlet of the mixing vessel, to form a closed apparatus therebetween.

The present invention is also directed to a method for homogenizing an aerosol formulation in a closed continuous-loop system under elevated pressure, the method including the steps of determining a desired level of homogenization, mixing an aerosol formulation in a mixing vessel, circulating the mixed aerosol formulation through a high pressure homogenizer, operating the high pressure homogenizer at a pressure sufficient to achieve homogenization of the mixed aerosol formulation, circulating the aerosol formulation back into the mixing vessel and repeating the aforementioned steps until the desired level of homogenization is achieved.

The closed continuous loop system may be connected by connecting means and conduit means to a high pressure filling station to fill aerosol containers. In an alternative embodiment, the closed continuous loop system may be used to prepare a concentrated aerosol formulation which is transferred by connecting means and conduit means to a large vessel where it is diluted with the aerosol propellant to a predetermined volume of aerosol formulation.

Accordingly, it is an object of the present invention to provide an improved method and system for homogenizing volatile mixtures.

It is a further object of the present invention to provide a method and system for homogenizing volatile mixtures, such as aerosol formulations comprising low boiling HFA propellants, at ambient temperature.

It is a still further object of the present invention to provide a method and system which permit the preparation of aerosol formulations comprising a wide range of surfactants, including those surfactants which would not be miscible in the formulation if processed at reduced temperature.

It is yet another object of the present invention to provide a method and system which can both micronize particles of active substance in an aerosol formulation and homogenize the formulation, eliminating the need for prior milling of the active substance.

Other objects of the present invention will become more readily apparent upon a review of the following detailed description of a preferred embodiment of the present invention, in conjunction with the accompanying drawings.

BRIEF DESCRIPTION OF THE DRAWINGS

The structure, operation and advantages of this invention will become further apparent upon consideration of the following non-limiting description of several embodiments of the resent invention in conjunction with the accompanying drawings, herein.

DETAILED DESCRIPTION OF THE INVENTION

Figure 1:
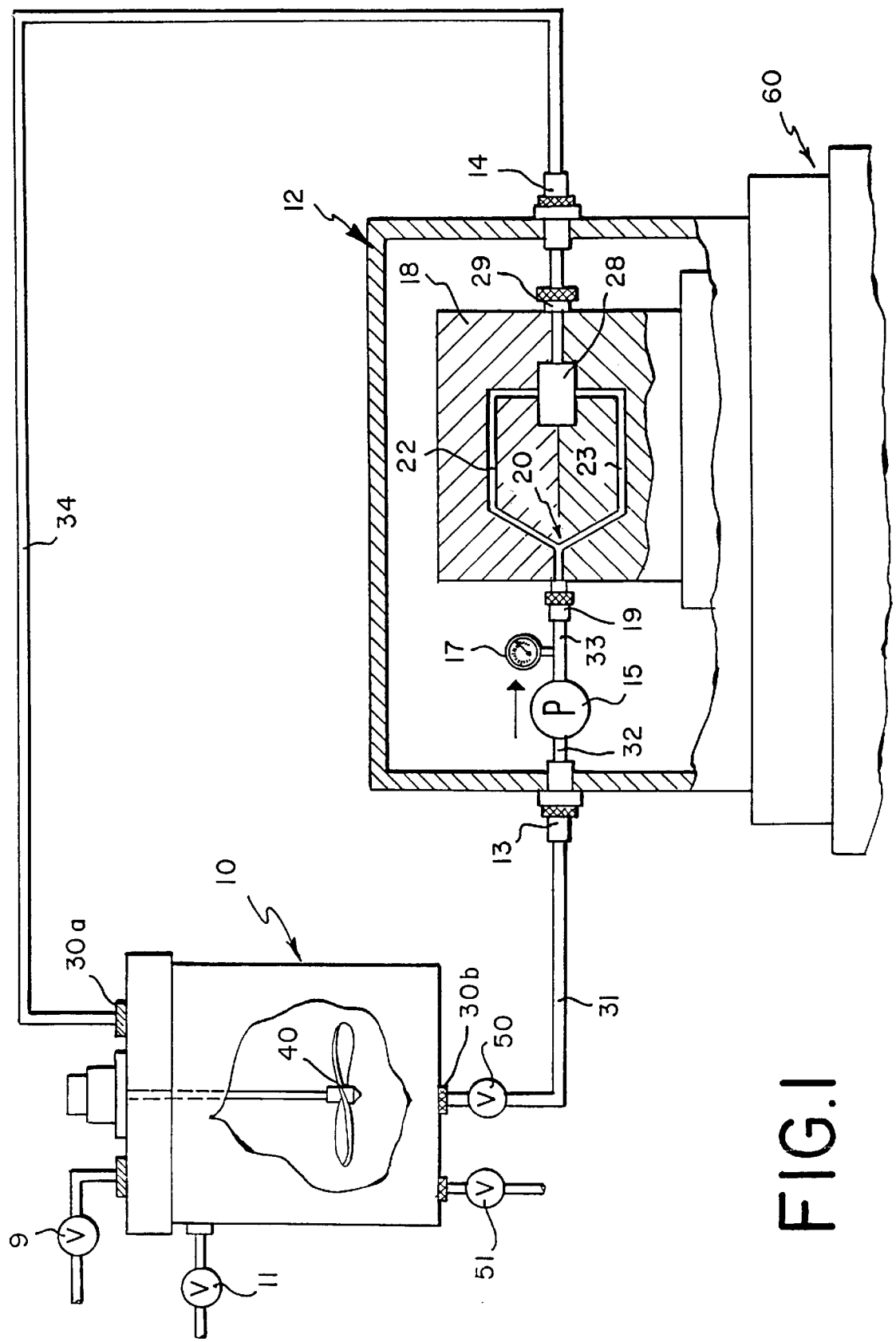
FIG. 1 is a schematic drawing of a closed, continuous-loop apparatus in accordance with the invention.

Referring to FIG. 1, a first embodiment of the system of the present invention is shown. In general, the system comprises a mixing vessel 10 that is provided with mixing means 40, a high pressure homogenizer 12 and connectors 30(a) and 30(b) which connect the mixing means 40 components through conduits 31, 32, 3, and 34 to form a closed, continuous-loop apparatus. Once sealed, the entire apparatus is adapted to operate under pressure, so that an aerosol formulation comprising a volatile propellant may be processed by the apparatus at ambient temperature.

The mixing vessel 10 is configured to accommodate an aerosol formulation and has a removable top which allows the mixing vessel to be charged. The mixing vessel 10 may be, for example, a Parr Model 4550 one gallon stirred floor stand reactor.

The high pressure homogenizer 12 operates upon an aerosol formulation at a pressure sufficient to achieve homogenization and, where applicable and desired, the simultaneous micronization of solid particles present in the aerosol formulation. The high pressure homogenizer 12 may be, for example, a Microfluidics Model M-110F Microfluidizer®. The apparatus and method of operation of a Microfluidizer® is further described in detail in U.S. Pat. No. 4,533,254 issued to Cook et al. on Aug. 6, 1985 and U.S. Pat. No. 4,908,154 issued to Cook et al. on Mar. 13, 1990, which are hereby incorporated by reference.

A brief description of the operation of the homogenizer 12 follows. The homogenizer 12, which has an inlet 13 and an outlet 14, relies on high pressure pump 15, having a pressure monitoring gauge 17 mounted on the outlet conduit 16, to propel material under pressure through a jet interaction chamber block means 18. Particle reduction, dispersion, and homogenization mechanisms occur within the interaction chamber 18. The jet interaction chamber block means 18 makes use of three different forces to achieve the necessary results: shear, impaction, and cavitation.

As the liquid stream is propelled at high pressure into the interaction chamber 18, the liquid stream enters an interaction chamber inlet 19 and is split into two laminar streams 22 and 23 by stream splitter 20. Each stream enters into channels in the jet interaction chamber block (not shown). The channels are formed by machining grooves into two opposed and closely fitted blocks. Shearing forces are applied to the liquid stream along the walls of the channels. The channels are configured to draw the respective laminar streams away from one another and then toward one another. Streams 22 and 23 converge at impaction chamber 28, and impact upon each other at high pressure in a space that has a cross-sectional area and volume that is relatively larger than that of the two channels. This rapid change in cross-sectional area and volume causes cavitation in the fluid stream. Moreover, the impaction results from the collision of the two streams with each other at high pressure and high velocity. The resulting stream is homogenized and any solid particles present in the formulation are micronized. The resulting stream exits the interaction chamber 18 at interaction chamber outlet 29 and is returned to mixing vessel 10 through connector 14 to conduit 30.

A homogenizer having the above described structure will micronize organic pharmaceutical compounds which are suspended in a liquid. The degree of homogenization or particle size reduction can be controlled by the energy input from the pump 15, the size of the channels 22 and 23 and the length of time that the liquid stream which contains the solid particles is cycled through the system. Other factors which determine the effect of the process are related to the inherent nature of the specific material being processed e.g. hardness, viscosity, etc.

The components of the closed apparatus are connected by connectors 30(*a*) and 30(*b*), which are compatible with apparatus pressures and the constitutents of the aerosol formulation. Connectors 30(*a*) and 30(*b*) may be, for example, stainless steel, plastic or rubber tubing. Each of the connectors 30(*a*) and 30(*b*) may optionally be terminated with "quick connect" couplings, so that the apparatus may be ready assembled and disassembled.

Connectors 30(*a*) and 30(*b*) serve as means to connect the conduits to the elements of the apparatus.

In use, the active ingredient and any necessary surfactant or other formulation components, aside from the volatile component are added to the mixing vessel 10. Typically, the mixing vessel 10 will have a sealable detachable lid which may be removed to allow convenient introduction of the these formulation components into the vessel. Once these non-volatile components have been introduced, the mixing vessel 10 is sealed.

The active ingredient may include for example, a pharmaceutically effective amount of a pharmaceutically active respiratory compound. Active ingredients include, for example, ipratropium bromide and albuterol sulfate. The active ingredient can be in a micronized or unmicronized form.

Possible surfactants include, for example, isopropylmyristate, acetylated monoglycerides such as Myvacet® 9-08, perfluorocarboxylic acid, polyethyleneglycol (PEG 200, 300, 400 or 600), polyethylene oxide sorbitan fatty acid ester (Tween® 20, 40, 60, 65 80 or 85), sorbitan esters, such as sorbitan monolaurate, sorbitan monooleate, sorbitan monopalmitate, and the like, polyvinylpyrrolidone (K-17: K-25: K-30 or K-90), propylene glycol and oleic acid. The surfactant may be added in an amount of 0.1% to 0.5% by weight based on the total weight of the composition or more. The total amount of surfactant should be less than about 3% w/w.

Where the aerosol formulation is sensitive to moisture and air, it may be necessary to purge the apparatus with ultrahigh purity nitrogen prior to loading the formulation to the mixing vessel.

A propellant is supplied to the reaction vessel 10, under pressure, through a valved inlet 11. The propellant may be, for example, a low boiling hydrocarbon; an HFA propellant such as HFA-227 (1,1,1,3,3,3-heptafluoropropane) HFA-134a (tetrafluoroethane) or a combination of HFA-227 and HFA-134a; or a CFC propellant such as CFC 12 or 114, or a mixture thereof. The propellant may additionally comprise a solvent, such as for example an alcohol such as ethanol.

In the process of the invention, a product concentrate can be made, but, depending upon the circumstances, need not be made. When working with small, lab-scale batches (approximately 3 liters of formulation), it is convenient to skip the step of creating a product concentrate and to directly homogenize the formulation components with an amount of the propellant which is sufficient to make up the complete formulation. For large scale batches (e.g., greater than 3 liters) it is preferred to make a homogenous product concentrate and then suitably dilute it with additional propellant.

Once all of the components of the aerosol formulation are in the mixing vessel 10 and the mixing vessel is pressurized to about 70 to 80 psi, the aerosol formulation is ready for mixing, homogenization and micronization. Mixing is accomplished by means of a stirrer 40, which is disposed within the mixing vessel 10. The stirrer 40 may preferably be set to a rate of 30 about 400 rpm. Once the contents of the mixing vessel have been thoroughly mixed, and with the stirrer still in operation, the outlet valve 50 is opened and formulation is allowed to circulate through the apparatus in the following sequence: from the mixing vessel 10, formulation flows through valve 50, connector 30(a), homogenizer 12, and then back through connector 30(b) to the mixing vessel 10. Mixing vessel 10 is optionally provided with drain 51 to facilitate cleaning of the mixing vessel or removal of residual product.

A formulation may comprise:

| | |
|---|---|
| ipratropium bromide, (micronized) | 45.0 g |
| isopropyl myristate | 75.0 g |
| 1,1,1,2,3,3,3-heptafluoropropane | 74.88 g* |

*This quantity includes an average of propellant introduced during processing to compensate for vapor which remains in the sealed manufacturing tank as the liquid bulk suspension is depleted during filling.

Ultra high purity nitrogen may be added to the mixing vessel 10 through valve 9 to bring the reaction vessel pressure up to about 100 psi. This excess pressure assists in the circulation of the aerosol formulation through the apparatus.

Where the active ingredient used as a starting material is a liquid or a solid which is already micronized, the high pressure homogenizer 12 operates upon the aerosol formulation at a pressure sufficient to achieve homogenization of the aerosol formulation. Where the active ingredient used as a starting material is an unmicronized solid, the high pressure homogenizer 12 operates upon the aerosol formulation at a pressure sufficient to achieve simultaneous micronization and homogenization of the aerosol formulation.

The pressures used for homogenization and simultaneous micronization and homogenization are dependent in part on the active ingredient itself. Certain active ingredients may require higher pressures and longer processing times to achieve desired results due to the inherent nature of their crystal structure.

For example, where micronized active ingredient is used as a starting material, the high pressure homogenizer 12 is typically set to supply a pressure of about 8,000 to 9,000 psi upon the aerosol formulation. Alternatively, if unmicronized active ingredient is used as a starting material, the means for high pressure homogenization and micronization 12 is typically set to provide a pressure of about 20,000 psi upon the aerosol formulation.

The aerosol formulation circulates until a desired level of homogenization and, if applicable, micronization is achieved. Typically, this will require the passage of a minimum of 10 volume exchanges through the apparatus.

During operation of the high pressure homogenizer 12, means 60 may be provided for cooling the high pressure homogenizer 12. The means 60 may be, for example, an ice bath or refrigeration unit. This is done to prevent excessive heat build-up that may result from the high velocity particle-particle impaction occurring within the high pressure homogenizer 12. The cooling means 60 reduces the temperature and pressure of the high pressure homogenizer 12 in order to maintain pressure below about 150 psi. In one embodiment, the cooling means 60 reduces the homogenizer temperature to about 16° C. and the pressure to about 85 psi while the high pressure homogenizer and micronizer 12 is in use. When the homogenization or the simultaneous micronization and homogenization process is complete, the aerosol formulation is ready for the dispensing process. Completed aerosol formulation may be dispensed into containers in two different ways. Where the completed formulation will not be harmed by cold, the formulation may be chilled to below its boiling point and then removed from the pressurized homogenization apparatus of the invention and, while still working at reduced temperature, filled into open containers which are then capped. The removal from the pressurized system of the invention may be effected by connecting the outlet of the mixing vessel 10 to a suitable dispenser which will deliver aliquots of the aerosol composition to aerosol containers which are capped and sealed using conventional techniques.

Alternatively, where chilling the formulation will cause a reduction in the amount of surfactant that is soluble in the formulation, filling of the containers must be carried out at ambient temperature and elevated pressure using a closed system. Another embodiment of the invention, described below, is adapted to perform this latter function.

Figure 2:
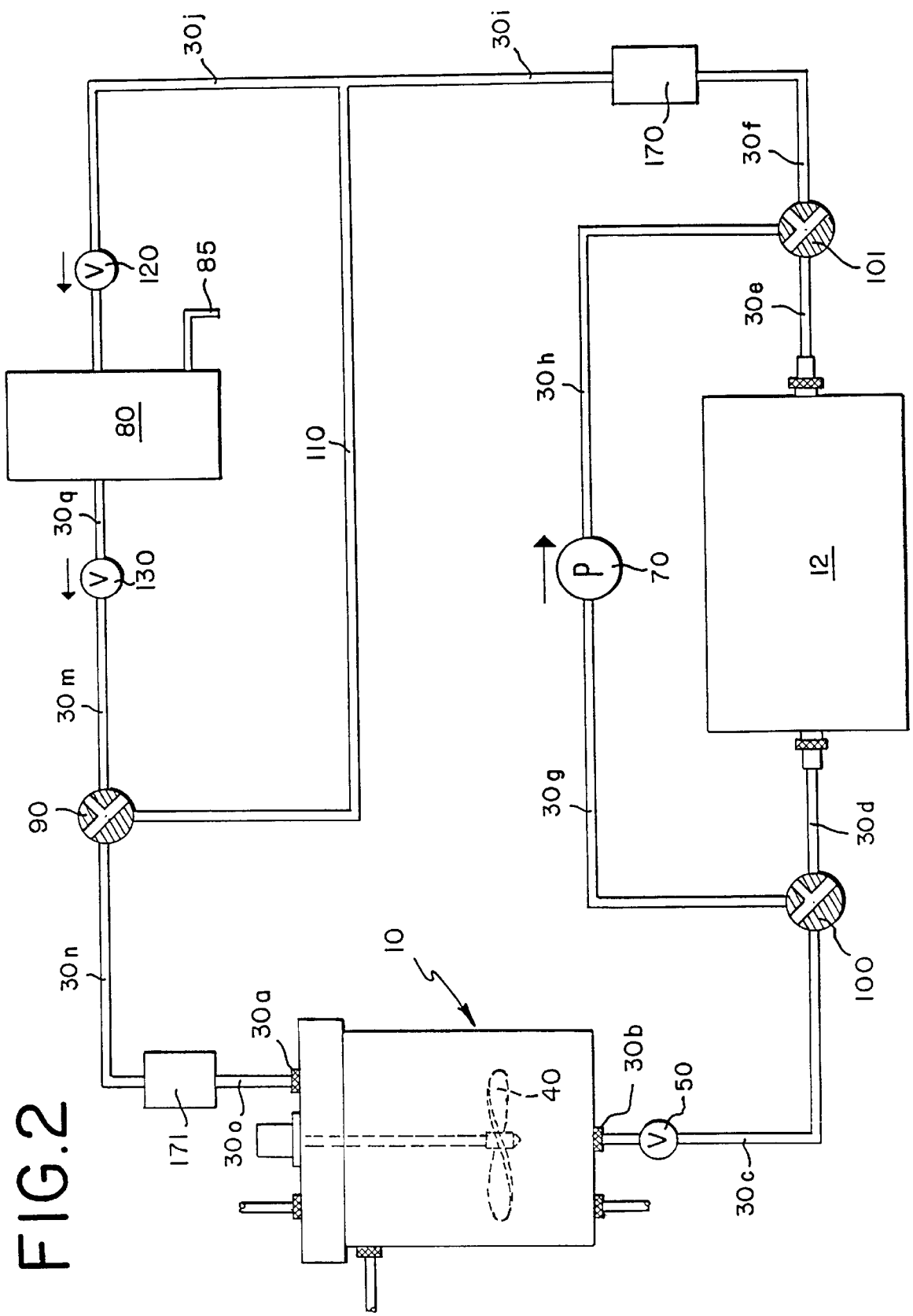
FIG. 2 is a schematic drawing of a closed, continuous-loop apparatus in accordance with the invention, adapted for dispensing an aerosol formulation into containers.

Referring to FIG. 2, a second embodiment of the invention is depicted. This is similar to the first embodiment but includes additional means for dispensing homogenized and, if applicable, micronized aerosol formulation into containers that have been sealed by crimping, while working under elevated pressure, by backfilling through the valves of capped containers. Common reference numerals refer to similar items and operate as described above. For example, with continuing reference to FIG. 2, in addition to a mixing vessel 10, a high pressure homogenizer 12, and connectors 30(a) and 30(b), as described above, the apparatus further comprises a three-way valve 100, a pump 70, another three-way valve 101, a by-pass conduit loop 110, an inlet check valve 120, a dispenser 80, an outlet check valve 130 and a pneumatic by-pass valve 90. Optionally, the apparatus may further comprise in-line flow meters 170 and 171 to monitor the flow of the formulation throughout the processing loop.

The pump 70 constitutes a means for circulating aerosol formulation through the apparatus during periods of apparatus operation when the formulation is shunted away from the homogenizer and micronizer 12. The pump 70 may be, for example, a Micropump® Model 152-000 magnetic pump. The by-pass conduit loop 110 provides a path through which the aerosol formulation may circulate when it is not being diverted to the dispenser 80. The by-pass conduit loop 110 may be made from stainless steel tubing or from plastic or rubber tubing which is inert to the materials which are being processed.

The dispenser 80 is a means for dispensing an aerosol formulation into aerosol containers. The dispenser 80 may be, for example, a Pamasol® 2016/1 pressure filler.

The in-line flow meter 170 may be located immediately after the three-way valve 100 and another in-line flow meter 171 may be located immediately prior to the reaction vessel 10.

With the exception of the transfer of fully processed formulation into containers that have been sealed by crimping, the operation of the apparatus provided by the second embodiment of the invention is essentially the same as that of the first embodiment. That is to say, the apparatus is charged with active ingredient, propellant and other formulation constituents, and the formulation is homogenized and, if applicable, solid active ingredient is micronized, in the same manner described above with reference to the first embodiment. The apparatus provided by the second embodiment differs from the first only in that additional elements are included which permit fully processed formulation to be diverted away from the homogenizer 12 and toward the dispenser 80, by means of which the formulation may be filled into containers.

While carrying out the process of homogenization, or simultaneous homogenization and micronization, aerosol formulation flows through the components of the embodiment shown in FIG. 2 in the following sequence: starting from the mixing vessel 10, the formulation flows through the drain valve 50, conduit 30(*c*), the three-way valve 100, conduit 30(*d*), the high pressure homogenizer 12, the conduit 30(*e*), the three-way valve 101, conduit 30(*f*), the optionally present flow meter 170, conduit 30(*i*), by-pass connector 110, open by-pass valve 90, conduit 30(*n*), the optionally present flow meter 171, conduit 30(*o*), and then back into the mixing vessel 10.

Once homogenization and, if applicable, micronization is complete, the flow of formulation is diverted from the homogenizer 12, to the pump 70, by way of conduit 30(*g*) and conduit 30(*h*), by operation of the three-way valves 100 and 101. The high pressure homogenizer 12 is removed from the circulation path of the aerosol formulation to avoid over-processing of the aerosol formulation. Up to this point the pump of high pressure homogenizer 12 is responsible for the circulation of formulation through the apparatus. Once the flow of formulation is diverted from the high pressure homogenizer 12, the pump 70 takes over this task. The pump 70, as well as the stirrer 40 of the reaction vessel 10, impart sufficient agitation to maintain suspension. Preferably, after about 15 minutes of circulation by the pump 70, when both the temperature and the pressure within the vessel increase to values which are close to their starting values, dispensing may begin.

Dispensing of the formulation is controlled by the coordinated operation of the two check valves 120 and 130 and the pneumatic by-pass valve 90.

To begin the dispensing process, the inlet check valve 120 and the outlet check valve 130 are opened and the pneumatic by-pass valve 90 is set so that the by-pass 110 is closed off which permits formulation to flow through conduit 30(*j*), and the valve 120, filling the dispenser 80 with a preset volume of formulation. Once filled, excess formulation exits the dispenser 80 and flows back to the reaction vessel 10, by way of the conduit 30(*q*), the open check valve 130, conduit 30(*m*), by-pass valve 90, conduit 30(*n*), optional flow meter 171 and conduit 30(*o*).

The aerosol formulation is filled into aerosol containers which have been capped and have suitable valves. The valve of a container to be filled is pressed into fluid-communicating connection with a valved port 85 of the dispenser 80. This causes the preset volume of formulation present in the dispenser 80 to be ejected from the dispenser 80 and back-filled through the valve of the container.

When the valve of a container is pressed into fluid-communicating connection with the port 85 of the dispenser 80, the inlet check valve 120 and the outlet check valve 130 are automatically closed, and the pneumatic by-pass valve is automatically reset to permit passage of formulation through the by-pass 110. Thus, the flow of formulation is shunted away from the dispenser 80 while it is filling a container.

Figure 3:
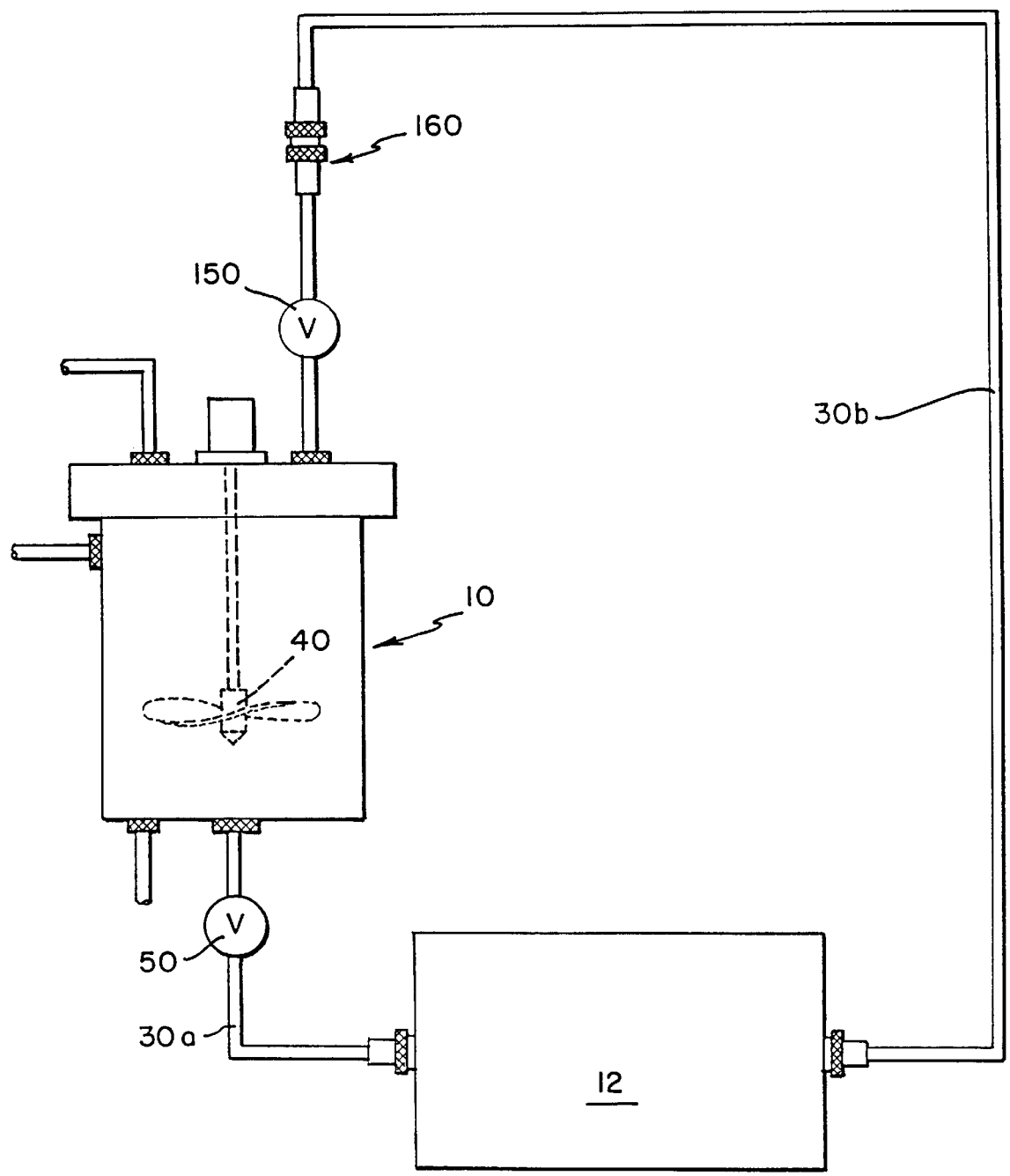
FIG. 3 is a schematic drawing of a closed, continuous-loop apparatus in accordance with the invention, adapted for industrial scale batch manufacturing.

Removal of a filled container from fluid communicating connection with the port 85 of the dispenser 80 causes the two check valves 120 and 130 to automatically open, while the pneumatic by-pass valve 90 closes to permit formulation to flow through the dispenser 80. This recharges the dispenser 80 with a preset amount of formulation, preparing it to fill another container. FIGS. 3 amd 4 together illustrate another embodiment of the invention which is specifically adapted for the production of large or industrial scale batches of aerosol formulation. Common reference numerals refer to similar items and operate as described above. For example, the apparatus of the invention for industrial scale batch manufacturing and dispensing comprises: a mixing vessel 10 having a mixing paddle 40; a drain valve 50; a conduit 30(*a*); a high pressure homogenizer 12; an additional conduit 30(*b*); a return-line coupler 160; and a return-line valve 150.

Figure 4:
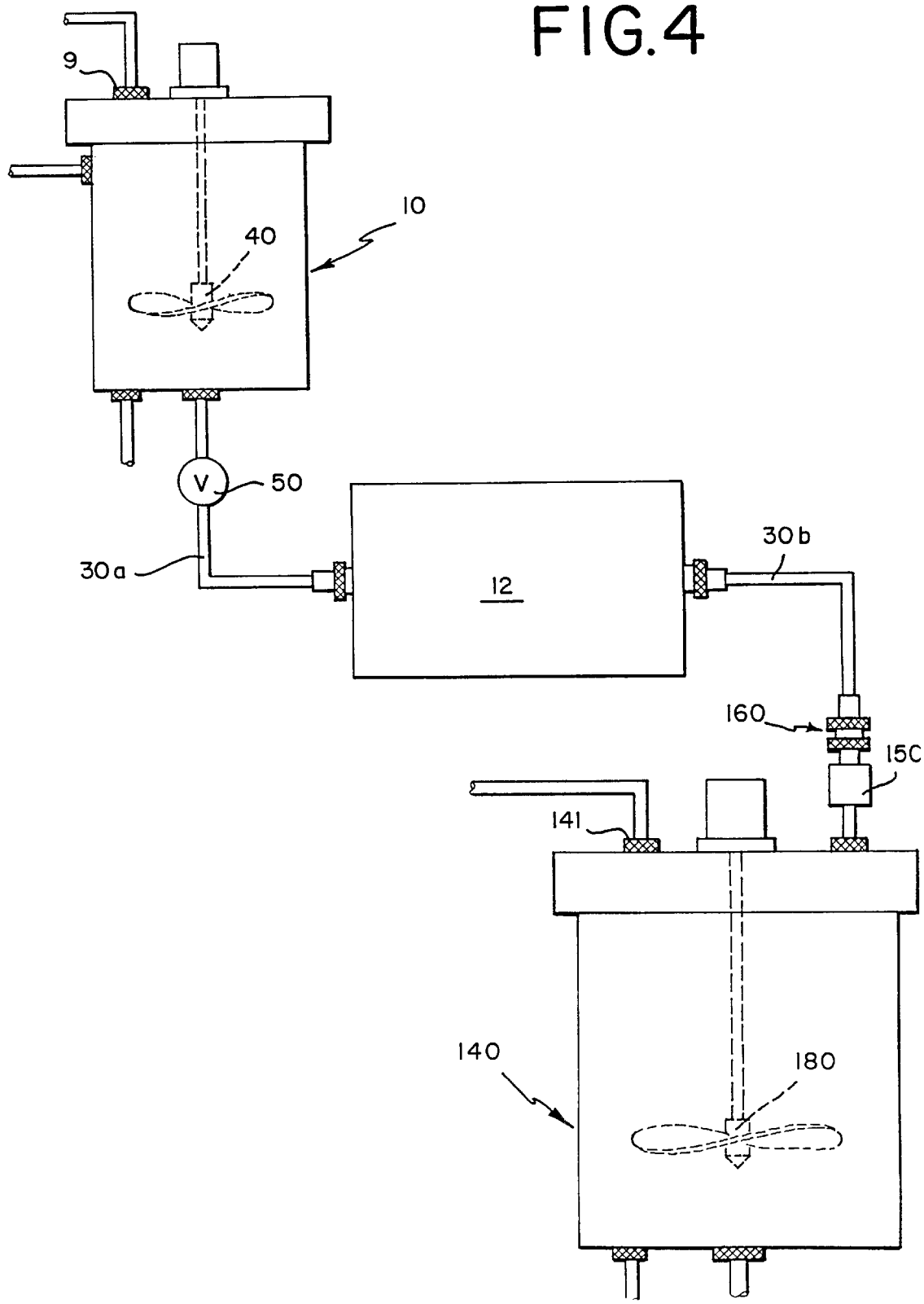
FIG. 4 is a schematic drawing of a closed apparatus in accordance with the invention, adapted for industrial scale dispensing of an aerosol formulation into containers.

As shown in FIG. 4, a formulation vessel 140 holds the aerosol formulation for the dispensing process. The formulation vessel 140 may be for example a closed stainless steel container.

A return-line coupler 160 is a means for coupling one end of the conduit 30(*b*) to either the the reaction vessel 10 (as shown in FIG. 3) or the formulation vessel 140 (as shown in FIG. 4). The coupler 160 may, for example, constitute a set of so-called quick connect couplers, wherein a male coupler will be used to terminate the conduit 30(*b*) and corresponding, mateable female couplers will be present as ports into the vessels 10 and 140.

The return-line valve 150 constitutes a means for shutting off the flow of formulation when the conduit 30(*b*) is not connected to either of the vessels 10 or 140, as when the connection is being switched from one to the other. As so-called quick connector couplers include integrated valves which automatically close when the two halves of the coupling are separated, the return-line valve 150 may conveniently be included as an intergral part of the coupling means 160.

The homogenization and, if applicable, the micronization of an aerosol formulation may be carried out using the embodiment of the invention depicted by FIGS. 3 and 4 in substantially the same way as with the embodiment depicted by FIG. 1. That is to say, the reaction vessel 10 is filled with a desired quantity of active ingredient (which, if a solid, may be either micronized or unmicronized), and any surfactants, solvents or other non-volatile components which are to be present in the formulation. Then the vessel 10 is sealed and propellant is introduced, under pressure, by means of the valved port 11. In the case of the production of large or industrial scale batches, however, it is preferred to introduce less than the full amount of propellant needed to constitute a complete formulation. Thus, it is preferred to initially create a product concentrate, which, due to its relatively modest volume, can be processed by the homogenizer 12 more readily than a complete formulation containing a full amount of propellant. Homogenization and, if applicable, micronization is carried out with the apparatus configured as shown in FIG. 3, which is functionally equivalent to the apparatus depicted by FIG. 1. Operation of the apparatus, configured as shown in FIG. 3 is substantially the same as the operation of the embodiment depicted in FIG. 1.

For the dispensing process, the drain valve 50 of the reaction vessel 10 is closed to the high pressure homogenizer 12. The micronized and homogenized aerosol formulation is then transferred to a formulation vessel 140 by the procedure described as follows.

The return-line valve 150 between the high pressure homogenizer 12 and the reaction vessel 10 is closed. The high pressure homogenizer 12 is terminated. All the aerosol formulation should be in the reaction vessel 10. The return-line coupler 160 is disengaged from the reaction vessel 10.

Referring to FIG. 4, the return-line coupler 160 is connected to the formulation vessel 140. The drain valve 50 is opened to the high pressure homogenizer 12 and the high pressure homogenization and micronization is initiated. The aerosol formulation is transferred at elevated pressure from the reaction vessel 10 to the formulation vessel 140. The stirrer 180 of the formulation vessel 140 is initiated. When most of the aerosol formulation has been transferred, the drain valve 50 of the reaction vessel 10 is closed and the high pressure homogenization unit 12 is terminated.

A rinsing procedure preferably follows. An amount of propellant for rinsing the mixing vessel 10, preferably less than 3 liters in the case of a 3.8 L mixing vessel, is added to the mixing vessel 10. This rinsing volume of propellant is stirred in the mixing vessel 10, preferably for about 5 minutes. The drain valve 50 of the reaction vessel 10 is opened to the high pressure homogenizer 12 and the high pressure homogenizer 12 is started. The high pressure homogenizer 12 pumps the rinsing volume of propellant into the formulation vessel 140. Several more of these rinsing procedures may preferably take place. Preferably, at least 4 rinsing procedures are utilized place. When rinsing is complete, the remaining amount of propellant required to bring the aerosol formulation to the final aerosol formulation is quantitatively added to the formulation vessel 140, working under pressure, by means of a valved inlet port 141. The stirrer 180 in the formulation vessel 140 continues to operate.

The aerosol formulation in the formulation vessel can now be filled into individual containers using the techniques described before. That is to say, while working at ambient pressure but at a temperature below the boiling point of the propellant and dispensed, the formulation can be transfered from the vessel 140 to open containers which can then be sealed with cap and valve assemblies. Alternatively, while working at ambient temperature and elevated pressure, the formulation in the vessel 140 can be filled into capped containers, using a dispenser means such as the means 80 incorporated into the embodiment depicted in FIG. 2.

A variety of aerosol formulations have been made using this industrial scale batch manufacturing process. For example, aerosol formulations of ipratropium bromide/HFC-227 and aerosol formulations of albuterol sulfate/HFC-227 have been manufactured using the process of this invention. In addition, an aerosol formulation of ipratropium bromide/HFC-227 using unmicronized active ingredient has also been manufactured using the process of this invention.

The following examples further describe and demonstrate preferred embodiments within the scope of the present invention. Although, these examples pertain to aerosol formulations for medicinal applications, the invention may also be suitable for applications in other industry e.g. paint, cosmetics, and deodorants. These examples are given for the purpose of illustration and are not to be construed as limitations of the present invention as many variations thereof are possible without departing from its spirit and scope.

EXAMPLES 1–4

The following Examples 1–4 illustrate MDI formulations prepared from the following ingredients, where micronized active ingredient was used as the starting material, using the method and apparatus of the invention and referring to FIG. 2:

| EXAMPLE | ACTIVE INGREDIENT | SURFACTANT | PROPELLANT |
| --- | --- | --- | --- |
| 1 | micronized ipratropium bromide | — | HFC-227 |
| 2 | micronized albuterol sulfate | — | HFC-227 |
| 3 | micronized ipratropium bromide | isopropylmyristate | HFC-227 |
| 4 | micronized ipratropium bromide and micronized albuterol sulfate | oleic acid, span, and isopropylmyristate | HFC-227 |

The active ingredient was added in an amount, that was calculated to privude a therapeutic dose when the composition is placed in an aerosol container with a metered valve, with any necessary surfactan to reaction vessel 10. The surfactant was added in an effective amount which is less than about 3% w/w. The reaction vessel was sealed and ultra high purity nitrogen was added to the sealed reaction vessel 10. The ultra high purity nitrogen was added to bring the final reaction vessel pressure to 50 psi. The ultra high purity nitrogen slowly purged the pressure within the reaction vessel 10. When the reaction vessel pressure was reduced to 10 psi, the purging was stopped.

The propellant was supplied to the reaction vessel 10. Ultra high purity nitrogen was added to the reaction vessel 10 to bring the reaction vessel pressure up to 100 psi. The stirrer 40 of the reaction vessel 10 was initiated and set to a rate of 400 rpm. Stirring continued for about 15 minutes before the subsequent steps. While the stirrer 40 was still operating at 400 rpm, the drain valve 50 of the reaction vessel 10 was opened to the high pressure homogenizer 12. A small amount of distilled $H_2O$ was placed in the intensifier pump of the high pressure homogenizer 12 to lubricate the seals. The water that was added did not noticeably increase the water content of the manufactured aerosols nor has it had an adverse effect on the initial stability of the formulations. For the homogenization process, the high pressure homogenizer 12 was set to supply a pressure of 8,000 psi upon the aerosol formulation.

The aerosol formulation was circulated through the following components in sequence: a reaction vessel 10; a drain valve 50; conduit 30(*c*); a three-way valve 100; conduit 30(*d*); a high pressure homogenizer 12; conduit 30(*e*); another three-way valve 101; conduit 30(*f*); the optional flow meter; conduit 30(*i*) either a by-pass loop 110 or conduit 30(*j*) and inlet check valve 120, a dispenser 80 and an outlet check valve 130; an conduit 30(*m*); a pneumatic by-pass valve 90; conduit 30(*n*); and back into the reaction vessel 10, where the stirrer 40 continued to operate. This was the complete circulation path of the aerosol formulation for the homogenization process. The entire apparatus was closed to the outside environment.

A processing time of 10 volume exchanges was carried out. An ice bath was maintained in the heat exchanger that is part of the high pressure homogenizer and micronizer 12 during the operation of the homogenizer 12. The vessel temperature was thereby reduced to 16° C. and the pressure maintained at 85 psi during the operation of the high pressure homogenizer 12.

The dispensing process followed. The high pressure homogenizer 12 was removed from the circulation path by diverting the three-way valve 100 from the high pressure homogenizer 12 to the pump 70. For the dispensing process, the pump 70 circulated the aerosol formulation through the following components in sequence: a reaction vessel 10; a drain valve 50; a conduit 30(*c*); a three-way valve 100; a conduit 30(*g*); a pump 70; a conduit 30(*h*); another three-way valve 101; a conduit 30(*f*); the optional flow meter 170; conduit 30(*i*) either a by-pass loop 110 or an inlet check valve 120, a dispenser 80, a conduit 30(*q*) and an outlet check valve 130, a conduit 30(*m*); a pneumatic bypass valve 90; a conduit 30(*n*); and back into the reaction vessel 10. This was the complete circulation path of the aerosol formulation for the dispensing process.

The aerosol formulation was circulated for 15 minutes by the pump 70. The aerosol formulation was then dispensed into MDI cans. These containers were already capped and crimped with suitable valves. As the aerosol formulation circulated, a container with a crimped valve was placed under valve port 85 of the dispenser 80. A preset volume of the aerosol formulation was delivered to the container. When the valve port 85 was depressed onto a valve of a container, the inlet check valve 120 and outlet check valve 130 was automatically closed and the pneumatic by-pass valve 90 opened to provide a path for the aerosol formulation still being circulated through the apparatus.

EXAMPLES 5–8

The following Examples 5–8 illustrate MDI formulations prepared from the following ingredients, where unmicronized active ingredient was used as the starting material, using the method and apparatus of the invention and referring to FIG. 2:

| EXAMPLE | ACTIVE INGREDIENT | SURFACTANT | PROPELLANT |
|---|---|---|---|
| 5 | unmicronized ipratropium bromide | — | Freon 12/114 blend |
| 6 | unmicronized ipratropium bromide | soy lecithin | Freon 11, Freon 12 and Freon 114 blend |
| 7 | unmicronized ipratropium bromide | — | HFC-227 |
| 8 | unmicronized albuterol sulfate | — | HFC-227 |

The active ingredient and any necessary surfactant was added to the reaction vessel 10. The surfactant was added in an amount preferably less than about 3% w/w. The reaction vessel was sealed and ultra high purity nitrogen was added to the sealed reaction vessel 10. The ultra high purity nitrogen was added to bring the final reaction vessel pressure to 50 psi. The ultra high purity nitrogen slowly purged the pressure within the reaction vessel 10. When the reaction vessel pressure reduced to 10 psi, the purging was stopped.

The propellant was supplied to the reaction vessel 10. Ultra high purity nitrogen was added to the reaction vessel 10 to bring the reaction vessel pressure up to 100 psi. The stirrer 40 of the reaction vessel 10 was initiated and may to a rate of 400 rpm. Stirring continued for about 15 minutes before the subsequent steps. While the stirrer 40 was still operating at 400 rpm, the drain valve 50 of the reaction vessel 10 was opened to the high pressure homogenizer 12. A small amount of distilled $H_2O$ was placed in the intensifier pump of the high pressure homogenizer 12 to lubricate the seals. The water that was added did not noticeably increase the water content of the manufactured aerosols nor has it had an adverse effect on the initial stability of the formulations. For the simultaneous micronization and homogenization process, the high pressure was set to provide a pressure of 20,000 psi upon the aerosol formulation.

The aerosol formulation was circulated through the following components in sequence: a reaction vessel 10; a drain valve 50; a conduit 30(*c*); a three-way valve 100; a conduit 30(*d*); a high pressure homogenizer 12; a conduit 30(*e*); another three-way valve 101; a conduit 30(*f*); the optional flow meter 170; conduit 30(*i*); either a by-pass loop 110 or conduit 30(*j*) and an inlet check valve 120, a dispenser 80 and a conduit 30(*q*), an outlet check valve 130; a conduit 30(*m*); a pneumatic by-pass valve 90; a conduit 30(*n*); and back into the reaction vessel 10, where the stirrer 40 continued to operate. This was the complete circulation path of the aerosol formulation for the simultaneous micronization and homogenization process. The entire apparatus was closed to the outside environment.

A processing time of 10 volume exchanges is used. An ice bath was maintained in the heat exchanger that is part of the high pressure homogenizer 12 during the operation of the homogenizer 12. The vessel temperature was thereby reduced to 16° C. and the pressure maintained at 85 psi during the operation of the high pressure homogenizer 12.

The dispensing process followed. The high pressure homogenizer 12 was removed from the circulation path by diverting the three-way valve 100 from the high pressure homogenizer 12 to the pump 70. For the dispensing process, the pump 70 circulated the aerosol formulation through the following components in sequence: a reaction vessel 10; a drain valve 50; a conduit 30(*c*); a three-way valve 100; a conduit 30(*g*); a pump 70; a conduit 30(*h*); another three-way valve 101; a conduit 30(*i*); either a by-pass loop 110 or a dispenser 80 as previously described.

The aerosol formulation was circulated for 15 minutes by the micropump 70. The aerosol formulation was then dispensed into MDI cans. These containers were already capped and crimped with the suitable valves. As the aerosol formulation was circulated, a container with a crimped valve was placed under the valve port 85 of the dispenser 80. A preset volume of the aerosol formulation was delivered to the container. When the dispenser 80 was depressed onto a valve of a container, the inlet check valve 120 and outlet check valve 130 was automatically closed and the pneumatic by-pass valve 90 opened to provide a path for the aerosol formulation still being circulated through the apparatus.

Figure 5:
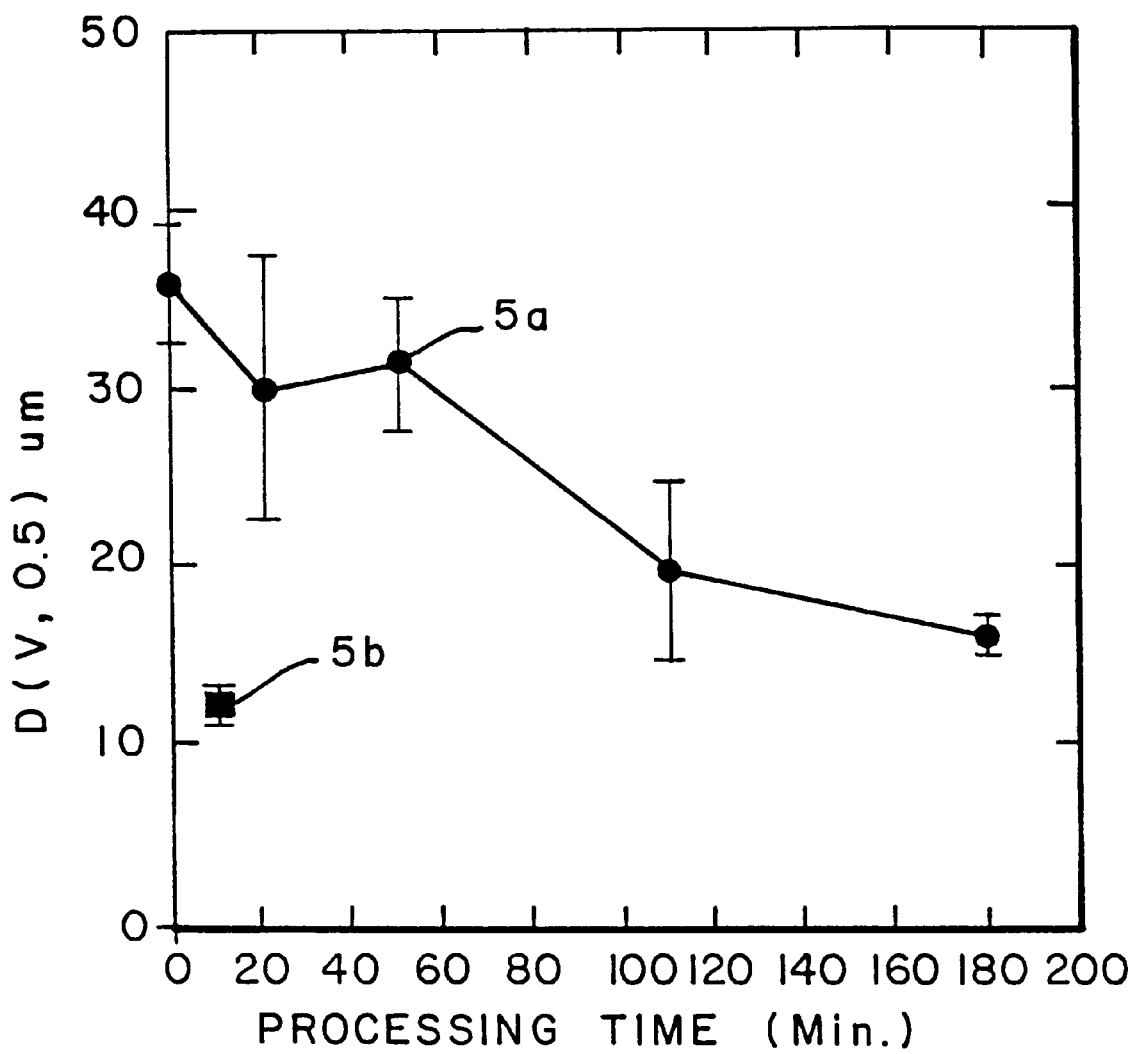
FIG. 5 is a graphical depiction of the mean particle diameter versus process time for an exemplary formulation containing previously unmilled particles of active substance, which has been treated by an apparatus in accordance with the invention, to thereby acheive both homogenization and micronization of the formulation.

COMPARATIVE EXAMPLE 4

Where a Microfluidics Microfluidizer® was used as the high pressure homogenizer and micronizer 12 for homogenization, the resulting product had a particle size distribution similar to those of aerosol formulations prepared using conventional stator-rotor homogenization methods. A graphical depiction of the mean particle diameter versus the fluidizer process time for this comparative example is shown in FIG. 5.

Figure 6:
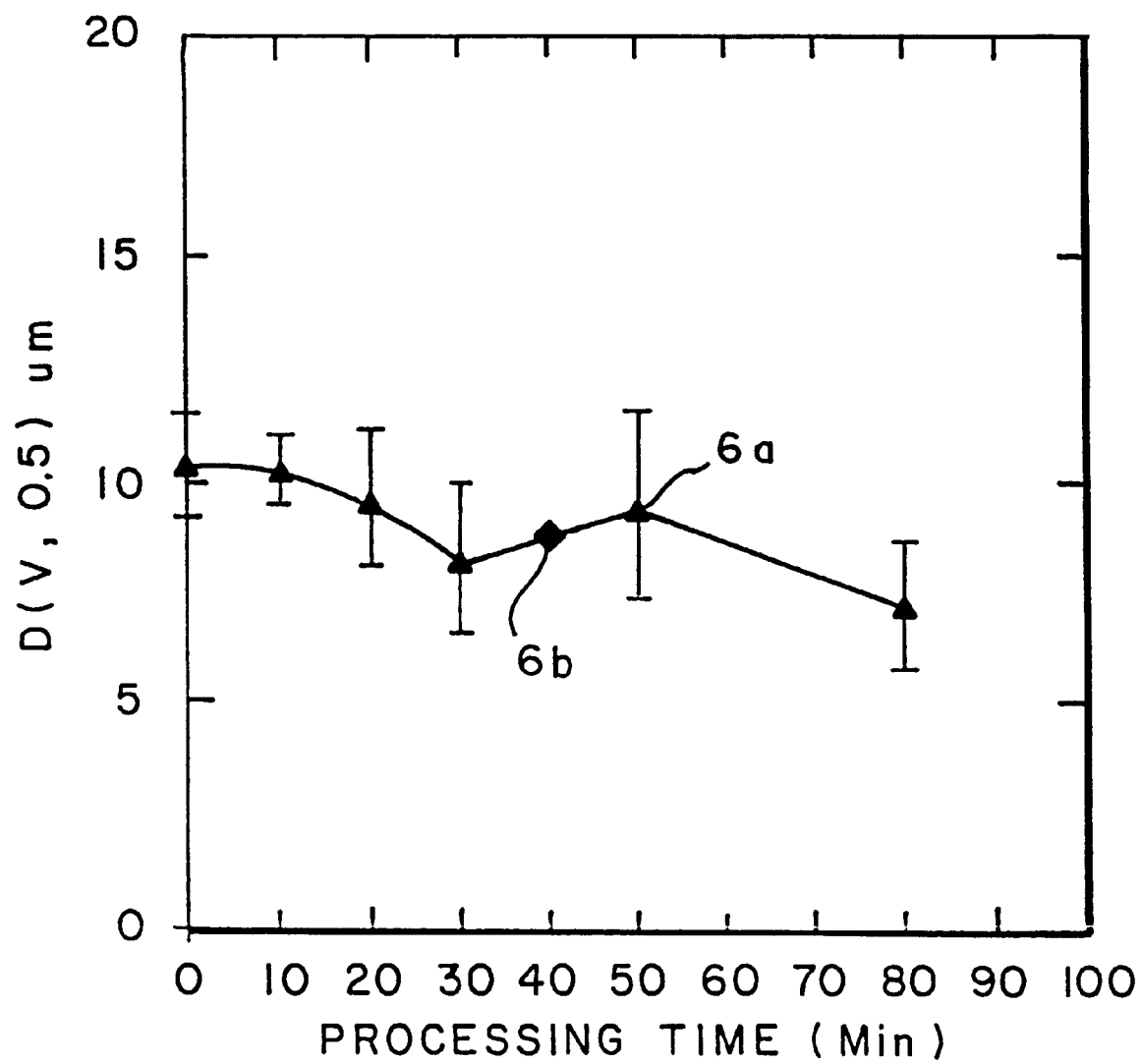
FIG. 6 is a graphical depiction of the mean particle diameter versus process time for an exemplary formulation containing previously milled particles of active substance, which has been treated by an apparatus in accordance with the invention, to thereby acheive homogenization but not micronization of the formulation.

As can be seen from FIG. 6 which plots the mean particle volume diameter vs. fluidizer process time when the fluidizer is run at 8K psi for homogenization. The triangles 6*a* represent a CFC product prepared with the fluidizer and the diamonds 6*b* represent a CFC product prepared using a rotor/stator homogenizer. When an already micronized active ingredient is used, particle size distribution is not adversely affected by the homogenizer and micronizer 12 to effect homogenization. Rather, the particle size distribution is substantially the same as when a rotor/stator homogenizer is used.

COMPARATIVE EXAMPLE 5

When a Microfluidics Microfluidizer® was used as the high pressure homogenizer and micronizer 12 to micronize unmicronized active ingredient, the primary particle size of the active ingredient was reduced by 30% to values which were comparable to those obtained for aerosol formulations where micronized active ingredients were used as the starting material. Particles having sizes within the range of 12 µm to 15 µm were produced by this method. A graphical depiction of the mean particle volume diameter versus fluidizer process time is shown in FIG. 5. The round dots 5a represent a product prepared with a fluidizer using an unmicroized active ingredient and the square 5b represents a commercial CFC product prepared using a rotor/stator.

As can be seen from FIG. 6, when an unmicronized active ingredient is used, particle size is beneficially reduced when the homogenizer 12 is used to effect homogenization. Moreover, particle size is unaffected by the use of a rotor/stator apparatus for homogenization.

Although the invention has been described in conjunction with specific embodiments, it is to be understood that many alternatives and variations will be apparent to those skilled in the art in light of the foregoing description. For example, although the preferred embodiment of the present invention is directed to a apparatus and method for homogenizing an aerosol formulation using a HFC propellant, the apparatus and method of the present invention may be used with any volatile mixture in which one component has a low-boiling point. Accordingly, the invention is intended to embrace all of the alternatives and variations that fall within the spirit and scope of the appended claims. The references referred to in this application are hereby incorporated by reference.

We claim:

1. A closed apparatus for homogenizing a mixture containing at least one low-boiling chlorofluorocarbon component, comprising:
   a reaction vessel;
   a homogenizer disposed in fluid communication with said reaction vessel, said homogenizer comprising an interaction chamber and an intensifier pump, said interaction chamber comprising a stream splitter and an impaction chamber adapted to recombine streams of said mixture split by said stream splitter, said intensifier pump comprising a pumping mechanism adapted to propel said stream through said interaction chamber to homogenize said mixture upon said recombination of said stream;
   a fluid conduit disposed between said reaction vessel and said homogenizer forming a closed apparatus therebetween; and a second pump disposed in parallel with said interaction chamber, said second pump disposed in closed fluid communication with said closed apparatus via a first valve and a second valve, said first valve disposed on an inlet side of said interaction chamber, said second valve disposed on an outlet side of said interaction chamber, wherein said second pump disposed parallel with said interaction chamber provides a path for the mixture to by-pass said interaction chamber.

2. The closed apparatus of claim 1 wherein said interaction chamber further comprises a first micro-channel and a second micro-channel, each of said first and said second micro-channels disposed in cooperation with said stream splitter to receive a stream of said mixture.

3. The closed apparatus of claim 2 wherein said first micro-channel and said second micro-channel diverge from said stream splitter and converge toward said impaction chamber.

4. The closed apparatus of claim 2 wherein said first and said second micro-channels are disposed in fluid communication with said impaction chamber to deliver fluid thereto, and wherein said impaction chamber has a volume larger than the volume of said micro-channels.

5. The closed apparatus of claim 1 wherein said closed apparatus further comprises a second fluid conduit disposed between said homogenizer and said reaction vessel to deliver hemogenized fluid from said interaction chamber to said reaction vessel.

6. The closed apparatus of claim 1 further comprising:
   a by-pass valve disposed in fluid communication with said reaction chamber to provide a path for said mixture to circulate through said closed apparatus upon actuation of said by-pass valve.

7. An apparatus for homogenizing an aerosol formulation, the apparatus comprising:
   a mixing vessel;
   means for performing high pressure homogenization; means for connecting said reaction vessel and said means for performing high pressure homogenization at a pressure of about 20,000 psi in a closed continuous-loop apparatus; pump means for circulating an aerosol formulation through the apparatus;
   a by-pass loop including a pump for providing a path for the aerosol formulation to circulate around the means for performing high pressure homogenization; and
   dispensing means for dispensing the aerosol formulation;
   an inlet check valve, an outlet check valve, and a pneumatic by-pass valve such that when the inlet check valve and the outlet check valve are closed, the pneumatic by-pass valve opens to provide a path for the aerosol formulation to circulate around the dispensing means and through the apparatus.

* * * * *